United States Patent [19]

Starn

[11] Patent Number: 5,370,712
[45] Date of Patent: Dec. 6, 1994

[54] ALIPHATIC DIAMINES FOR DISTILLATE FUELS STABILIZATION

[75] Inventor: Roy E. Starn, West Chester, Pa.

[73] Assignee: E. I. Du Pont de Nemours and Company, Wilmington, Del.

[21] Appl. No.: 929,451

[22] Filed: Aug. 14, 1992

Related U.S. Application Data

[63] Continuation of Ser. No. 351,634, May 15, 1989, abandoned.

[51] Int. Cl.$^5$ .............................................. C10L 1/22
[52] U.S. Cl. ........................................................ 44/432
[58] Field of Search ........................................... 44/432

[56] References Cited

U.S. PATENT DOCUMENTS

| | | | |
|---|---|---|---|
| 2,672,408 | 3/1954 | Bonner | 44/72 |
| 2,681,935 | 6/1954 | Thompson | 44/72 |
| 2,945,749 | 7/1960 | Andrews, Jr. | 44/72 |
| 3,523,769 | 8/1970 | Tooke | 44/432 |
| 3,944,397 | 3/1976 | Gardiner et al. | 44/75 |
| 4,011,057 | 3/1977 | Sayers | 44/432 |
| 4,040,799 | 8/1977 | Alink et al. | 44/75 |
| 4,163,646 | 8/1979 | Oude Alink et al. | 44/73 |
| 4,166,726 | 9/1979 | Harle | 44/73 |
| 4,509,952 | 4/1985 | Braxton, Jr. | 44/57 |
| 4,647,289 | 3/1987 | Reid | 44/72 |
| 4,648,885 | 3/1987 | Reid | 44/57 |

*Primary Examiner*—Margaret Medley
*Attorney, Agent, or Firm*—Charles E. Feeny

[57] ABSTRACT

This invention relates to novel secondary diamine compounds which can be represented by the general formula:

$$R^1(R^2)HCHN-A-NHCH(R^2)R^1$$

wherein $R^1$ and $R^2$ are the same or different substituent comprising $C_nH_{2n+1}$ wherein $n=1$ to 6, and A is a branched-chain divalent saturated aliphatic radical containing 4 to 7 carbon atoms, particularly 1,5-diisopropyl-amino-2-methylpentane. It relates also to compositions containing said compounds which are useful for stabilizing hydrocarbon distillate fuel oils, hydrocarbon distillate fuel oils stabilized therewith, and to processes for stabilizing such oils.

4 Claims, No Drawings

ALIPHATIC DIAMINES FOR DISTILLATE FUELS STABILIZATION

This is a continuation of application Ser. No. 07/351,634 filed May 15, 1989, now abandoned.

FIELD OF THE INVENTION

This invention relates to novel secondary diamine compounds. It relates also to compositions containing said compounds which are useful for stabilizing hydrocarbon distillate fuel oils, hydrocarbon distillate fuel oils stabilized therewith. It relates in addition to processes for stabilizing such oils.

BACKGROUND OF THE INVENTION

Petroleum distillate fuel oils are susceptible to deterioration during storage or use. Discoloration and insoluble sludge, gum and sediment often result, making the fuel less acceptable to the customer since it is more apt to clog screens, filters, nozzles, etc., of equipment in which it is consumed. Resistance to discoloration and the accompanying formation of insolubles is, therefore, a desirable property of present day fuel oils, such as heating oils, diesel fuels and other hydrocarbon distillate fuels. Storage stability of distillate fuel oils is usually determined by accelerated tests which are carried out under oxidative conditions at elevated temperatures.

In the past, several types of additives, including a large number of different amines, have been reported as stabilizers for distillate fuel oils and other similar petroleum products. Chao et al., in U.S. Pat. No. 4,264,461 disclose stabilized hydrocracked lubricating oils containing aliphatic amines having the structure:

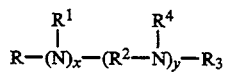

wherein R, $R^1$, $R^3$, and $R^4$ may be hydrocarbon; $R^2$ may be divalent hydrocarbon, and x and y are 0 to 10. Only a single aliphatic diamine is found among the specific compounds disclosed by Chao, viz. N-alkyl-1,3-propylene diamine (alkyl group derived from coconut oil fatty acids); all others are monoamines. Andress, in U.S. Pat. No. 2,945,749, discloses certain tertiary alkyl primary amines as stabilizers against color development and insolubles formation in fuel oils during storage. On the other hand, Bonner, in U.S. Pat. No. 2,672,408,and Alink et al., in U.S. Pat. No. 4,040,799, disclose secondary and tertiary amines as being effective in stabilizing fuels oils. Dunworth, in U.S. Pat. No. 3,490,882, and Braxton, Jr., in U.S. Pat. No. 4,509,952, disclose the use of tertiary amines for stabilizing distillate fuel oils.

BRIEF SUMMARY OF THE INVENTION

The present invention relates to novel compounds and compositions containing the same for the stabilization of hydrocarbon distillate fuel oils comprising aliphatic secondary diamines which, in relatively low concentrations, significantly retard discoloration and the formation of insolubles in fuel oils. The diamines of this invention may be used by themselves or in combination with other additives. This invention relates also to hydrocarbon distillate fuel oils which contain a small amount of one or more of the diamines of this invention effective to inhibit discoloration of, and sediment formation in, said oils during storage and use. It relates further to a process in which deterioration of hydrocarbon distillate fuel oils is inhibited by the addition thereto of a small but effective amount of one or more of the diamines of this invention.

DETAILED DESCRIPTION OF THE INVENTION

The present invention is based on the discovery that aliphatic secondary diamines which can be represented by the following general formula are unusually effective stabilizers for hydrocarbon distillate fuels:

wherein $R^1$ and $R^2$ are the same or different substituent comprising $C_nH_{2n+1}$ wherein n=1 to 6, and A is a branched-chain divalent saturated aliphatic radical containing 4 to 7 carbon atoms. The fuel compositions containing the novel compounds of this invention show significantly less insoluble residue formation and better color stability than untreated fuels during tests designed to simulate storage. The amount of the diamines of this invention effective to inhibit oxidation of hydrocarbon distillate fuel oils can be determined empirically. In general, an amount in the range between about 0.00003% and about 0.04% by weight, based on the fuel oil, is suitable; preferably one uses an amount in the range between about 0.0001% and about 0.004% of the diamine.

The diamines of this invention possess properties which enhance their usefulness as stabilizers for hydrocarbon distillate fuel oils. They are readily soluble in the fuel oils and have virtually no extractability from the fuel oils by water; they do not contribute to water-hazing or emulsification and are ashless. The diamines of this invention are also compatible with other additives normally associated with finished fuels, such as sludge dispersants, corrosion inhibitors and anti-hazing agents and may be used to advantage with one or more such materials. Examples of sludge inhibitors are oil-soluble copolymers having an addition-type polymeric main chain and a plurality of addition-type polymeric branches extending from the side thereof, disclosed in U.S. patent application Ser. No. 07/307,500, filed 8 Feb. 1989, the contents of which are incorporated herein by reference. Preferably the main polymer chain is derived from lauryl methacrylate, and the polymeric side branches are derived from dimethylaminoethyl methacrylate. In another embodiment of this invention, from about 10 to 90% by weight of a diamine of this invention is blended with about 10 to 90% by weight of an amine-containing copolymer as defined in the aforesaid application. In yet another embodiment of this invention, from about 85 to 97% by weight of a diamine of this invention is blended with about 3 to 15% by weight of an N,N'-di(o-hydroxyarylidene)-1,2-alkylenediamine metal deactivator in which the arylidene radical contains 6 to 7 carbon atoms and the alkylene radical contains 2 to 6 carbon atoms, e.g., 1,2-ethylene, 1,2-propylene or 1,2-cyclohexylene. Preferred metal deactivators are N,N'-disalicylidene-1,2-propylenediamine and N,N'-disalicylidene-1,2-cyclohexylenediamine. The diamine/amine-containing polymer compositions may also contain one or more of the folowing: 2 to 10% metal deactivator, 5 to 80% corrosion inhibitor and 5 to 50% antihaze agent (the latter may be amido-amine carboxylates, soluble quaternary ammonium salts, or polyoxyalkylene compounds).

The secondary diamines of this invention, and their combinations with the metal deactivators, sludge dispersants, antihaze agents, and/or the like, are soluble in fuel oils and may be added directly to the distillate fuel oil to be stabilized. Or, if desired, they may be added in the form of concentrates containing about 5 to 80% by weight of the additive or additive blend, the remainder being a normally liquid inert hydrocarbohn carrier solvent such as kerosene, xylene or the like.

The aliphatic secondary diamines of this invention can be prepared by a variety of methods known to those skilled in the art. Included in such methods, is the reductive alkylation of saturated aliphatic primary diamines using a catalyst, hydrogen and a ketone. When the reductive alkylation method is used, the branched-chain primary diamine preferred as starting material is 1,5-diamino-2-methylpentane because of availability, cost, excellent activity and low melting points of the product secondary diamines, and their ready solubility in not only the distillate fuels, themselves, but also in the solvents generally used to prepare stabilizing concentrates for distillate fuels. Acetone is the preferred carbonyl-containing reactant for the reductive alkylation because of cost, high performance of the resultant products and ease of procurement and operation. The most preferred secondary amine of this invention is 1,5-diisopropylamino-2-methylpentane (DIAMP). It is normally a liquid at ambient temperatures which is readily soluble in hydrocarbon solvents and distillate fuels; it has a low level of odor and is an especially effective stabilizer for a variety of distillate fuels at relatively low concentrations.

The quantity of diamines to be employed in practicing this invention will vary depending on the initial condition and degree of instability of the oil, and the effect desired. While they may be used in the proportion of about 0.1 to 130 pounds per 1,000 barrels (ptb) of fuel oil, normally about 1 to 10 ptb are used.

Broadly, the distillate fuels are mixtures of hydrocarbons boiling in the range of about 400° to about 1000° F., which mixtures are normally susceptible to deterioration with the formation of colored bodies and insoluble sludge and sediment under thermal and oxidative conditions. The present invention is particularly concerned with stabilizing such products as diesel engine fuels for stationary, marine, automotive and locomotive type engines (described in ASTM specification D-975); domestic and industrial heating oils (described in ASTM specification D-396); and stationary gas turbine fuels (described in ASTM specification D-2880). Included are straight run fuel oils, thermally cracked, catalytically cracked, thermally reformed, and catalytically hydrocracked stocks, and blends thereof as known and commonly employed in the art.

The following examples are given in further illustration of the invention but not by way of limitation (in the Tables, "L" means lighter and "D" darker than).

EXAMPLE 1

A stainless steel Parr bomb was charged with 122 g (2.1 mole) acetone, 116 g (1.0 mole) 1,5-diamino-2-methyl-pentane and 4.0 g of 1% platinum on carbon catalyst containing 46% solids. The bomb was pressurized to about 500 psig with hydrogen and heated to 125°±5° C. while maintaining the hydrogen pressure. The contents of the bomb were agitated for about 30 minutes after hydrogen absorption ceased. After cooling to room temperature, the catalyst was separated from the contents of the bomb by filtration and the solvent removed in a rotary evaporator at about 10 mm pressure. Gas chromatography indicated that the remaining 146 g of 1,5-diisopropylamino--2-methylpentane (DIAMP) was 99% pure.

EXAMPLE 2

Several accelerated storage tests were run comparing DIAMP as prepared in Example 1, with N,N-dimethyl-cyclohexylamine (DMCHA) as stabilizers for a variety of typically unstable fuel blends of catalytically or thermally cracked distillates with straight run fuel oil or kerosene. The tests were carried out by a "300° F. Accelerated Fuel Oil Stability Test", which evaluates the effectiveness of additives in inhibiting residue formation and color degradation of distillate fuels. The Test consists of aging a sample of the test distillate fuel containing the additive at 300° F. for 90 minutes, cooling the sample to room temperature, and collecting any insoluble residue by vacuum filtration through a white filter paper or blotter. The resultant filter pad was then evaluated using a test method which measured the amount of light reflected from the filter pad by the use of a reflectance meter. The greater the amount of colored insolubles collected on the filter pad, the lower will be the reflectance. The color of the test distillate fuel was also determined by ASTM Method D1500 before and after storage; the lighter the color, the lower will be the ASTM D1500 reading. The additives were tested at concentrations of 2 and 6 pounds per thousand barrels (ptb) of fuel. A control, containing no additive, was included in each set of tests for comparison.

TABLE 1

| Fuel | Original Color D-1500 | Additive Type | Conc. ptb | Aged Fuel Color D-1500 | Pad Rating % Reflectance |
|---|---|---|---|---|---|
| A | 1.0 | None | — | 7.5 | 42 |
| " | | DMCHA | 2 | 3.0 | 82 |
| " | | DIAMP | 2 | 2.0 | 88 |
| " | | DMCHA | 6 | L2.5 | 88 |
| " | | DIAMP | 6 | 2.0 | 88 |
| B | L2.0 | None | — | 7.5 | 69 |
| " | | DMCHA | 2 | L6.0 | 79 |
| " | | DIAMP | 2 | 5.0 | 84 |
| " | | DMCHA | 6 | L4.0 | 88 |
| " | | DIAMP | 6 | L3.5 | 90 |
| C | L3.5 | None | — | 5.0 | 39 |
| " | | DMCHA | 2 | 5.0 | 43 |
| " | | DIAMP | 2 | 5.0 | 50 |
| " | | DMCHA | 6 | 5.0 | 45 |
| " | | DIAMP | 6 | L5.0 | 64 |
| D | L3.0 | None | — | L5.0 | 20 |
| " | | DMCHA | 2 | 4.5 | 17 |
| " | | DIAMP | 2 | L5.0 | 35 |
| " | | DMCHA | 6 | L5.0 | 36 |
| " | | DIAMP | 6 | 4.5 | 35 |

The results in Table 1 demonstrate that DIAMP is superior to the prior art DMCHA both in stabilizing color and in inhibiting insolubles formation, especially at lower concentrations, in the variety of distillate fuel oils tested.

EXAMPLE 3

DIAMP was also evaluated against DMCHA in a "175° F. (80° C.) Accelerated Fuel Oil Stability Test" using a storage period of 7 days at 175° F. The amount of sediment formed during storage was determined gravimetrically and was reported as percent reduction versus the amount of sediment formed in the untreated control test fuel oil. In this evaluation, the higher the reduction in the amount of sediment, the more effective is the additive as a stabilizer. The results in Table 2 again demonstrate the superiority of DIAMP over the prior art DMCHA.

TABLE 2

| Fuel | Original Color D-1500 | Additive Type | Conc. ptb | Aged Fuel Color, D-1500 | Aged Fuel Sediment % Reduction |
|---|---|---|---|---|---|
| A | 1.0 | None | — | L4.5 | — |
| " | | DMCHA | 2 | 3.5 | 68 |
| " | | DIAMP | 2 | L3.0 | 86 |
| " | | DMCHA | 6 | L3.5 | 79 |
| " | | DIAMP | 6 | L3.0 | 87 |
| D | 2.5 | None | — | 3.5 | — |
| " | | DMCHA | 2 | L3.5 | 18 |
| " | | DIAMP | 2 | L3.5 | 37 |
| " | | DMCHA | 6 | 3.0 | 29 |
| " | | DIAMP | 6 | 3.0 | 73 |
| E | 2.0 | None | — | 6.0 | — |
| " | | DMCHA | 2 | 6.0 | 30 |
| " | | DIAMP | 2 | 6.0 | 41 |
| " | | DMCHA | 6 | 5.5 | 28 |
| " | | DIAMP | 6 | 5.5 | 53 |
| F | L1.5 | None | — | L4.0 | — |
| " | | DMCHA | 2 | 5.0 | 43 |
| " | | DIAMP | 2 | L3.0 | 73 |
| " | | DMCHA | 6 | 5.0 | 45 |
| " | | DIAMP | 6 | 2.5 | 73 |
| G | L3.0 | None | — | L5.5 | — |
| " | | DMCHA | 2 | L5.5 | 2 |
| " | | DIAMP | 2 | L5.5 | 43 |
| " | | DMCHA | 6 | L5.5 | 18 |
| " | | DIAMP | 6 | 5.0 | 61 |
| H | L1.0 | None | — | 4.0 | — |
| " | | DMCHA | 2 | 3.0 | 63 |
| " | | DIAMP | 2 | 2.0 | 84 |
| " | | DMCHA | 6 | L3.0 | 73 |
| " | | DIAMP | 6 | 2.0 | 81 |

EXAMPLE 4

The efficacy of DIAMP as a stabilizer for distillate fuel oils was also evaluated versus N-coco-1,3-propylenediamine (CPD) and N,N-dibutylamine (DBA), using the same tests as were used in Example 3. The results, set forth in Table 3, indicate DIAMP is superior to both of these prior art stabilizers.

TABLE 3

| Fuel | Original Color D-1500 | Additive Type | Conc. ptb | Aged Fuel Color, D-1500 | Aged Fuel Sediment % Reduction |
|---|---|---|---|---|---|
| B | L2.0 | None | — | D8.0 | — |
| " | | CPD | 2 | D8.0 | 38 |
| " | | DBA | 2 | D8.0 | 8 |
| " | | DIAMP | 2 | D8.0 | 81 |
| " | | CPD | 6 | D8.0 | 38 |
| " | | DBA | 6 | 7.0 | 92 |
| " | | DIAMP | 6 | 5.0 | 96 |
| M | 2.0 | None | — | 5.0 | — |
| " | | CPD | 2 | L5.0 | 22 |
| " | | DBA | 2 | L5.0 | 18 |
| " | | DIAMP | 2 | L5.0 | 59 |
| " | | CPD | 6 | L5.0 | 47 |
| " | | DBA | 6 | L5.0 | 31 |
| " | | DIAMP | 6 | 4.5 | 68 |
| J | 3.5 | None | — | L8.0 | — |
| " | | CPD | 2 | L8.0 | 0 |
| " | | DBA | 2 | L8.0 | −4 |
| " | | DIAMP | 2 | 7.5 | 20 |
| " | | CPD | 6 | L8.0 | 11 |
| " | | DBA | 6 | 7.5 | −2 |
| " | | DIAMP | 6 | L7.5 | 46 |
| G | 4.0 | None | — | 6.0 | — |
| " | | CPD | 2 | L6.0 | −4 |
| " | | DBA | 2 | L6.0 | −6 |

TABLE 3-continued

| Fuel | Original Color D-1500 | Additive Type | Conc. ptb | Aged Fuel Color, D-1500 | Aged Fuel Sediment % Reduction |
|---|---|---|---|---|---|
| " | | DIAMP | 2 | L6.0 | 6 |
| " | | CPD | 6 | L6.0 | −5 |
| " | | DBA | 6 | L6.0 | −3 |
| " | | DIAMP | 6 | L6.0 | 22 |
| K | L5.5 | None | — | D8.0 | — |
| " | | CPD | 2 | D8.0 | −6 |
| " | | DBA | 2 | D8.0 | −7 |
| " | | DIAMP | 2 | D8.0 | 9 |
| " | | CPD | 6 | D8.0 | −4 |
| " | | DBA | 6 | D8.0 | −2 |
| " | | DIAMP | 6 | D8.0 | 24 |

The negative numbers in the above Table indicate that there was more sediment in the aged test sample containing the additive than in the control.

EXAMPLE 5

DIAMP was also compared to N,N-dimethylcocoamine (DMCA) in accordance with the test used in Examples 3 and 4. The data set forth in Table 4 shows that DIAMP was more effective than DMCA as a stabilizer in every fuel tested.

TABLE 4

| Fuel | Original Color D-1500 | Additive Type | Conc. ptb | Aged Fuel Color, D-1500 | Aged Fuel Sediment % Reduction |
|---|---|---|---|---|---|
| B | L2.0 | None | — | D8.0 | — |
| " | | DMCA | 3 | 7.0 | 89 |
| " | | DIAMP | 3 | L5.0 | 94 |
| M | 2.0 | None | — | 4.5 | — |
| " | | DMCA | 3 | L4.5 | 34 |
| " | | DIAMP | 3 | L4.5 | 59 |
| J | 4.0 | None | — | L8.0 | — |
| " | | DMCA | 3 | L8.0 | 0 |
| " | | DIAMP | 3 | 7.5 | 46 |
| L | L2.0 | None | — | 4.5 | — |
| " | | DMCA | 3 | L4.5 | 19 |
| " | | DIAMP | 3 | 3.5 | 37 |
| F | 1.5 | None | — | L3.5 | — |
| " | | DMCA | 3 | L3.5 | 21 |
| " | | DIAMP | 3 | 2.5 | 53 |

EXAMPLE 6

DIAMP was also evaluated against N,N'-dimethyl-2-methylpentylenediamine (DMAMP) as a stabilizer for distillate fuel oils in the same tests as described in Examples 2 and 3. The results contained in Tables 5 and 6 indicate clearly that DIAMP is superior to DMAMP as a distillate fuel oil stabilizer.

TABLE 5

| Fuel | Original Color, D-1500 | Additive Type | Conc., ptb | Aged Fuel Color, D-1500 | Aged Fuel Pad Rating, % Reflection |
|---|---|---|---|---|---|
| A | L1.5 | None | — | 6.0 | 25 |
| " | | DMAMP | 2 | L3.0 | 67 |
| " | | DIAMP | 2 | L2.5 | 80 |
| " | | DMAMP | 15 | 2.5 | 73 |
| " | | DIAMP | 15 | 2.0 | 77 |
| " | L1.5 | None | — | L5.0 | 39 |
| " | | DMAMP | 2 | L4.0 | 49 |
| " | | DIAMP | 2 | 3.0 | 56 |
| " | | DMAMP | 15 | L3.5 | 55 |
| " | | DIAMP | 15 | L3.0 | 62 |
| " | 1.0 | None | — | 7.0 | 34 |
| " | | DMAMP | 2 | 3.0 | 55 |
| " | | DIAMP | 2 | 2.5 | 65 |
| " | | DMAMP | 15 | L3.0 | 58 |

TABLE 5-continued

| Fuel | Original Color, D-1500 | Additive Type | Conc., ptb | Aged Fuel Color, D-1500 | Pad Rating, % Reflection |
|---|---|---|---|---|---|
| " | | DIAMP | 15 | L2.5 | 66 |
| M | L1.5 | None | — | 4.5 | 46 |
| " | | DMAMP | 2 | 3.5 | 61 |
| " | | DIAMP | 2 | L3.0 | 63 |
| " | | DMAMP | 15 | 3.0 | 60 |
| " | | DIAMP | 15 | 2.5 | 62 |
| N | 1.5 | None | — | L3.0 | 75 |
| " | | DMAMP | 2 | L3.0 | 68 |
| " | | DIAMP | 2 | 2.5 | 76 |
| " | | DMAMP | 15 | L3.0 | 71 |
| " | | DIAMP | 15 | L2.5 | 76 |

TABLE 6

| Fuel | Original Color, D-1500 | Additive Type | Conc., ptb | Aged Fuel Color, D-1500 | Sed., % Redn. vs. Control |
|---|---|---|---|---|---|
| A | L1.5 | None | — | L4.0 | — |
| " | | DMAMP | 2 | L3.5 | 49 |
| " | | DIAMP | 2 | L3.0 | 91 |
| " | | DMAMP | 15 | L4.0 | 62 |
| " | | DIAMP | 15 | L3.0 | 92 |
| F | L1.5 | None | — | L4.0 | — |
| " | | DMAMP | 2 | 3.0 | 35 |
| " | | DIAMP | 2 | L3.0 | 74 |
| " | | DMAMP | 15 | L3.5 | 43 |
| " | | DIAMP | 15 | L3.0 | 70 |
| H | 1.0 | None | — | 4.0 | — |
| " | | DMAMP | 2 | 3.0 | 52 |
| " | | DIAMP | 2 | 2.5 | 82 |
| " | | DMAMP | 15 | 3.0 | 60 |

TABLE 6-continued

| Fuel | Original Color, D-1500 | Additive Type | Conc., ptb | Aged Fuel Color, D-1500 | Sed., % Redn. vs. Control |
|---|---|---|---|---|---|
| " | | DIAMP | 15 | L2.5 | 84 |
| M | L1.5 | None | — | 3.5 | — |
| " | | DMAMP | 2 | L3.0 | 37 |
| " | | DIAMP | 2 | L2.5 | 76 |
| " | | DMAMP | 15 | L3.0 | 29 |
| " | | DIAMP | 15 | L2.5 | 71 |
| N | 1.5 | None | — | L5.0 | — |
| " | | DMAMP | 2 | 4.5 | 11 |
| " | | DIAMP | 2 | 4.5 | 41 |
| " | | DMAMP | 15 | L5.5 | −21 |
| " | | DIAMP | 15 | 4.5 | 48 |

It will be noted that in most of the Examples given in Tables 1–6 in which two treating levels were used, the lower treating level of DIAMP was more effective than the higher treating level of the prior art additive.

I claim:

1. A fuel composition comprising a distillate hydrocarbon fuel oil containing from about 0.00003% to about 0.04% by weight, based on the weight of the fuel oil, of 1,5-diisopropylamino-2-methylpentane.

2. The composition of claim 1 wherein the amount of said amine in said composition is in the range between about 0.0001% and about 0.004% by weight.

3. A process for stabilizing a distillate hydrocarbon fuel oil which comprises adding thereto from about 0.00003% to about 0.04% by weight, based on the weight of the fuel oil, of 1,5-diisopropylamino-2-methylpentane.

4. The process of claim 3 wherein the amount of said amine is in the range between about 0.0001% and about 0.004% by weight.

* * * * *